US006689748B1

(12) United States Patent
Theoharides

(10) Patent No.: US 6,689,748 B1
(45) Date of Patent: Feb. 10, 2004

(54) METHOD OF TREATING MAST CELL ACTIVATION-INDUCED DISEASES WITH A PROTEOGLYCAN

(75) Inventor: Theoharis C. Theoharides, 14 Parkman St., Brookline, MA (US) 02146

(73) Assignee: Theoharis C. Theoharides, Brookline, MA (US)

( * ) Notice: Subject to any disclaimer, the term of this patent is extended or adjusted under 35 U.S.C. 154(b) by 756 days.

(21) Appl. No.: 09/056,707

(22) Filed: Apr. 8, 1998

(51) Int. Cl.[7] .................. A61K 38/16; A61K 38/00; A01N 25/00
(52) U.S. Cl. .............. 514/8; 514/21; 514/826
(58) Field of Search ............... 424/282.1; 514/27, 514/21, 456, 826, 8, 56; 536/8

(56) References Cited

U.S. PATENT DOCUMENTS

| 5,250,529 A | * | 10/1993 | Theoharides | 514/255 |
| 5,260,335 A | * | 11/1993 | Wagner et al. | 514/532 |
| 5,648,355 A | * | 7/1997 | Theoharides | 514/255 |
| 5,980,865 A | * | 11/1999 | Ahmed | 424/45 |

OTHER PUBLICATIONS

Danielov, *Chemical Abstracts*, vol. 125, #132809, 1996.*
Theoharides et al. The Pharmacologist 39(4), Abs. 9700, Dec. 10, 1997, Meeting 4/18–22(1998).
Theoharides. The Mastocytosis Chronicles, 4(1):3 (Winter 1998).
Bauman, Urology Times, 26(3), Mar. 1998.
Theoharides et al., 1997 International Research Symposium on Interstitial Cystitis Abs. p. 35, Oct. 30–31 (1997).
Parsons et al. Brit J. Urol., 73:504 (1994) p. 504–507.
Porru et al., Urol. Int. 59: (1997). pp. 26–29.

* cited by examiner

*Primary Examiner*—Shengjun Wang
(74) *Attorney, Agent, or Firm*—Law Offices of Dr. Melvin Blecher; Melvin Blecher

(57) ABSTRACT

The invention provides a method for preventing and treating the harmful biological effects of biochemicals secreted from activated mast cells in the organism of warm blooded animals and more especially human beings, said effects being associated with allergy (including but not limited to allergic conjunctivitis, allergic rhinitis, allergic otitis, asthma, allergic uticaria, food allergy and atopic dermatitis), hyperproliferative diseases such as leukemia and systemic mastocytosis, interstitial cystitis, inflammatory bowel disease, irritable bowel syndrome, osteoporosis and scleroderma. The method consists in administering to said animals and especially to human beings an effective amount of a proteoglycan such as chondroitin sulfate with mast cell secretion inhibitory activity, alone or in combination with one or more synergistic adjuvants such those belonging to the class of flavonoids or compounds with histamine-1 receptor antagonist activity.

4 Claims, No Drawings

METHOD OF TREATING MAST CELL ACTIVATION-INDUCED DISEASES WITH A PROTEOGLYCAN

BACKGROUND INFORMATION

This invention relates to the treatment of diseases induced by biochemicals released from activated mast cells. More particularly, the invention relates to treatment of mast cell-induced diseases such as allergies, interstitial cystitis, inflammatory bowel disease, irritable bowel syndrome, and certain hyperproliferative diseases such as systemic mastocytosis with a proteoglycan without or with functionally synergistic flavonoids and/or heterocyclic antagonists of histamine receptors.

Mast cells are a normal component of connective and mucosal tissues and play an important role in allergy and inflammation. They are localized in the connective tissues, but also in the mucosa of the bladder, gastrointestinal tract, lung and nose, as well as in the skin and the meninges of the brain. They are located there because these tissues are the main entry points for infective organisms, allergens and other noxious chemicals that trigger the body's immune response.

Mast cells derive from the bone marrow and migrate into the tissues where they synthesize and can secrete numerous vasoactive, nociceptive and inflammatory mediators. (Galli, S. J. *N. Engl. J. Med.* 328:257, 1993). They are located perivascularly close to nerve endings and can be activated by a variety of neuroimmunoendocrine triggers. (Theoharides, T. C. *Int. J. Tissue React.* 18:1, 1996).

Mast cells are located at strategic points around capillaries and small blood vessels, where they are important in regulating the extent of constriction or dilation of the vessels including those which make up the blood-brain barrier, the protective lining of the brain which excludes toxic materials (Theoharides, T. C., *Life Sciences* 46:607, 1990).

Each mast cell contains up to 500 secretory granules, each storing more than 20 potent biological compounds. Mast cells secrete the contents of these granules (i.e., degranulate) when triggered by various specific and non-specific mechanisms, such as the allergic reaction involving immunoglobulin E (IgE) and antigen (Ag). Notable among non-allergic triggers are certain polysaccharides or monosaccharide-containing lectins such as dextran and concanavalin A (Baxter, J. H. et al, *Biochemical Pharm.* 27:497, 1978). Other known triggers include the neurotransmitter acetylcholine, various neuropeptides such as calcitonin-gene-related peptide (CGRP), corticotropin-releasing hormone (CRH), neurotensin (NT), substance P (SP), somatostatin and vasoactive intestinal peptide (VIP), as well as viruses, bacterial toxins, drugs (such as aspirin, morphine and curare), contrast media used in radiology, extreme heat, cold, solar radiation, hyperosmotic media and pressure (Theoharides, ibid.).

Compounds released by mast cell degranulation, collectively referred to as mediators or activators, include: histamine, kinins, prostaglandin $D_2$ and vasoactive intestinal peptide, which are vasodilatory, as well as serotonin, prostaglandin $F_2$-alpha and leukotrienes, which are vasoconstrictive. In addition, cytokines, histamine, kinins and prostaglandins can cause pain directly, while enzymes that destroy proteins and phospholipids can cause tissue damage directly. Finally, cytokines can cause inflammation and regulate other biological responses (Galli, S. J., above).

The compounds released by the mast cells following degranulation are known to cause many biological responses which are part of the overall response of the body to invasion by infective organisms, allergens or other stressful stimuli. Degranulation will be defined herein as the release of any or all mediators from any or all secretory granules, whether in parallel, sequentially, differentially or selectively. Relevant examples of such responses are vasodilation and recruitment of inflammatory cells (e.g. leukocytes) from the circulation, tearing, nasal secretions, bronchoconstriction, itching of the skin, diarrhea or bladder pain.

Histamine and the other mediators are secreted from the granules of mast cells during degranulation. The histamine and other mediators then bind to specific receptors on the surface of endothelial cells on vessels, neurons or other tissues. Vasodilation and chemoattraction permits lymphocytes to leave the blood circulation and enter the tissue, where they cause additional mast cell degranulation and other responses. The process of degranulation continues, eventually involving many mast cells. It is important to note that there are no clinically available drugs with mast cell secretion inhibitory activity. Anti-histamines, properly known as histamine receptor antagonists, act only after histamine is released (Theoharides, T. C., *Drugs* 37:345, 1989). They neither block the secretion of histamine or other mediators nor the action of any other mediators. Disodium cromoglycate (cromolyn) is called a "mast cell stabilizer" and is available for rhinitis, asthma and food allergies, but its action is short-lived, it is only partially effective, it does not affect all mast cells and it is difficult to put in solution (Shapiro, G. G. et al., *Pharmacotherapy* 5:156, 1985).

The common form of interstitial cystitis (IC) is the "early" or non-ulcer variety with normal bladder capacity and the absence of inflammation. The role of mast cells in the bladder has acquired increased significance since it was shown that mast cells in this tissue can be activated with or without an increase in their numbers (Theoharides, T. C. et al., *Sem. Urol.*, 9:74, 1991). Moreover, acute immobilization stress results in bladder mast cell degranulation (Spanos et al., *J. Urol.*,157:669, 1997).

Mucosal mast cells have also been implicated in irritable bowel syndrome (IBS) (Weston, A. P., et al., *Digestive Diseases and Sciences* 38:1590, 1993) where are increased in numbers and/or activated to various degrees. (Pang, X. et al., *Urology* 47:436, 1996). Moreover, histamine and prostaglandins have been involved in gastrointestinal permeability and related diarrhea syndromes. (Castaglluolo, I. et al., *Am. J. Physiol.* 271:884, 1996). Recent studies have shown that acute stress by immobilization leads to gastrointestinal mast cell activation, a process blocked by pre-treatment with neutralizing antiserum to corticotropin releasing hormone (CRH) which is liberated under stress (Castaglluolo, I. et al., above). We further showed that CRH can induce mast cell degranulation and increased vascular permeability directly (Theoharides, T. C., et al., *Endocrinology* 139:403, 1998).

The term inflammatory bowel disease (IBD) is used to describe a variety of disorders. Crohn's disease, as well as various forms of infectious diarrhea, such as that due to *Clostridium difficile* which is called pseudomembranous colitis, are the most common forms of inflammatory conditions of the intestine. Recent evidence (discussed above) indicates that mast cells exist in the mucosa of the small intestine and that they are different from mast cells in other, especially connective tissues. Moreover, they have also been shown to be in close apposition to nerve endings, suggesting that they may be affected by the nervous system. In fact, gastrointestinal membranes are activated in Crohn's disease (Dvorak et al., *Int. Arch. Allergy Immunol.*, 98:158, 1992).

Mast cell secretion was shown to be stimulated by parathyroid hormone (PTH) in vitro (Tsakalos, N. D. et al.,

*Biochemical Pharmacology* 32:355, 1983). In addition, PTH was shown to increase mast cell accumulation in bone (Rockoff, S. D. et al., *Calc. Tiss. Res.* 5:49, 1970). Molecules secreted from mast cells may increase bone resorption, leading to a net loss of bone loss, and eventually resulting in osteoporosis in susceptible individuals. In fact, osteoporosis was seen as the sole presentation of bone marrow mastocytosis in humans (Lidor, C., et al., *Journal of Bone and Mineral Research* 5:871–876, 1990). During an investigation of the bone response to calcium deficient diets over time, dramatic increases in the numbers of mast cells were observed in the metaphyseal region of tibia, which showed osteitis fibrosa, and eventually net loss of bone. Finally, there have been several recent case reports of systemic osteoporosis associated with systemic mastocytosis (Chines, A., et al., *Journal Clin. Endocrinol. Metab.*, 72:140, 1991;Longley et al., *J. Am. Acad. Dermatol.* 32:545, 1995).

Scleroderma is an autoimmune disease which occurs five times more often in women than men. It involves the whole body, but it primarily manifests itself on the skin which is progressively replaced by fibrotic tissue giving a hardened and aged appearance. Other peripheral manifestations are Raynaud's phenomenon, which is characterized by intense vasoconstriction of the hand vessels leading to anoxia and pain. Mast cells have often been associated with this disease (Siebold, J. R., et al., *Arthritis and Rheumatism* 33:1702, 1990;Irani, A-M., et al., *Arthritis and Rheumatism* 35:933, 1992). There is no effective therapy for this condition even though calcium entry blockers such as nifedipine and verapamil have been used.

Proteoglycans are high molecular weight polyanionic macromolecules (heteropolysaccharide) consisting of many different glycosaminoglycan chains linked covalently to a protein core that constitutes up to about 5% of the total macromolecules. Monosaccharide components of proteoglycans, such as glucosa nine sulfate or N-acetyl-D-glucosamine are also available commercially. Six distinct classes of proteoglycans are now recognized: chondroitin sulfate, dermatan sulfate, heparin and its sulfate, keratin sulfate, and hyaluronic acid. (For structures, see "Textbook of Biochemistry", T M Devlin, ed., John Wiley & Sons, N.Y., 1986, pp 347–351); Chondroitin sulfate, like the other proteoglycans, is naturally occurring, and is a natural constituent of connective tissues. It is available over the counter as a food supplement (e.g. INHOLTRA, Kennebunk, Me. 04043 or AMERIFIT, Bloomfield, Conn. 06002).

Flavonoids have been reported to inhibit mast cell secretion (Middleton, E. et al, *Biochem. Pharm.* 43:1167, 1992). However, the only patented use of flavonoids is the use of the flavonoid kaempferol for a dermatological preparation to stimulate skin pigmentation or superficial body growth (WO90/06104, Jun. 14, 1990). Flavonoids are naturally occurring molecules. The average daily U.S. diet contains about 1 g of mixed flavonoids. However, certain concentrated flavonoids are being sold over the counter as food supplements (e.g. pycnogenol, 25 mg capsules by Country Life, Hauppauge, N.Y. or quercetin 300 mg caplets by Allergy Research, Grove Calif. or Freeman Industries, Tuckahoe, N.Y.).

However, neither proteoglycans without or with flavonoids have been described for therapeutic use in any of the clinical conditions described above.

SUMMARY OF THE INVENTION

The invention provides a method for preventing and treating the harmful biological effects of secretion of biochemicals from mast cells in the organs of warm blooded animals and more especially human beings. These harmful biological effects include allergy (including butriot limited to allergic conjunctivitis, allergic rhinitis, allergic otitis, asthma, and atopic dermatitis) interstitial cystitis, inflammatory bowel disease, irritable bowel syndrome, scleroderma, osteoporosis, and hyperproliferative diseases such as systemic mastocytosis and leukemia.

In one aspect of the invention, the method consists of administering to said animals and especially to human beings an amount of a proteoglycan with mast cell secretion inhibitory activity, such as chondroitin sulfate, keratan sulfate, and dermatan sulfate.

In a second aspect of the invention, the method consists of administering a proteoglycan combined with one or more synergistic adjuvants (such as those belonging to the class of flavonoids (such as myrisetin, quercetin, genisetin or kaempferol) or heterocyclic compounds with histanine-receptor antagonist activity.

These and other aspects will become clear by reference to the specification and appended claims.

DESCRIPTION OF THE PREFFERED EMBODIMENTS

It has been unexpectedly discovered that diseases resulting from the biochemicals released from activated mast cells can be successfully treated with proteoglycans alone or together with one or more synergistic adjuvants such as flavonoids and heteroyclic compounds with histamine receptor antagonist activity.

The method of the present invention consists of the daily administration to patients suffering from an allergic condition of about 100 to about 5,000 mg of a proteoglycan such as chondroitin sulfate. The oral route of administration or local application to affected areas is preferred so that the patient can self-medicate.

In accordance with the present invention, proteoglycans may be administered to patients in any conventional oral or parenteral dosage form that will make the drug most available to exposed mucosal or skin surfaces. Oral dosage forms may include tablets, capsules, caplets, liquids and the like, including generally from about 200 to about 2,000 mg of chondroitin sulfate per dosage unit together with flavonoids and/or the heterocyclic compounds claimed and suitable pharmaceutically acceptable excipients, binders, sweeteners, coloring agents and other conventional additives. Parenteral dosage forms may include any conventional solutions of chondroitin sulfate, for example, an isotonic saline solution together with pharmaceutically acceptable preservatives and buffers. The parenteral dosage forms generally contain from about 50 to about 250 mg of chondroitin sulfate and may be administered with a dropper for allergic conjunctivitis, spray for allergic rhinitis, inhaler for allergic asthma, intravesically for interstitial cystitis, or with a cream or ointment for allergic dermatitis or allergic urticaria.

In one preferred method, a proteoglycan may be initially administered orally to patients in daily doses of about 500 mg each, with gradual increments up to a maximum of 2,500 mg b.i.d.

Where indicated, flavonoids or histamine recptor antagonists are administered together with a proteoglycan, at doses of about 2500 mg proteoglycan, about 500 mg flavonoid and/or about 50 mg of a histamine-1 receptor antagonist.

The method of the present invention also provides dramatic symptomatic relief for patients suffering from interstitial cystitis and irritable bowel syndrome even where conventional modalities of treatment have failed. Patients receiving chondroitin sulfate treatment experience a decrease in urinary and bowel movement frequency respectively and associated pain because of additive actions not found in any other approved or experimental medication: a) inhibition of secretion from mucosal mast cells that have been found to proliferate and be activated in the bladder wall of patients suffering from interstitial cystitis and the intestinal wall of patients suffering from irritable bowel syndrome b) forming a protective layer covering the mucosal surface of the bladder and the intestine.

The method of the invention can also be used to prevent or treat mast cell secretion-related diseases such as osteoporosis, scleroderma (or, systemic sclerosis). Further, the method of the invention can be used to treat hyperproliferative diseases involving mast cells, such as leukemia and systemic mastocystitis.

The following examples provides a detailed illustration of methods of administering the compound(s) as claimed in the present invention. These examples are not intended to limit or restrict the scope of the invention in any way, and should not be construed as providing dosage forms, regimens or methods of administration which must be utilized exclusively to practice the invention.

EXAMPLE 1

We studied the effect of chondroitin sulfate on histamine secretion from mast cells purified from peritoneal cavities of male Sprague/Dawley rats (300g, Charles River) over 25% Metrizamide (Accurate Scientific). Mast cells were preincubated with $10^{-5}$ M saccharide for 60 min at 37° C. followed by two washes and resuspension in saccharide-free medium prior to stimulation with $10^{-5}$ M of the mast cell secretagogue, compound 48/80 (C48/80) or the neuropeptide Substance P (SP). As the cells were washed free of saccharide, any inhibitory effect was not due to any interference with binding of C48/80 or SP to the cell surface. Consequently, this effect is distinct from reports showing that certain monosaccharide-containing lectins inhibit C48/80-induced mast cell secretion (Matsuda, K., et al., *Jpn. J. Pharmacol.* 64:1, 1994). The results show that chondroitin sulfate can powerfully inhibit mast cell activation as shown in Table 1.

TABLE 1

Inhibition of Mast Cell Secretion by Saccharides

| Saccharide | Mast Cell Secretion (% inhibition) | |
|---|---|---|
| | C48/80 (n = 4) | SP (n = 3) |
| D-Glucosamine sulfate (a) | 33.7 ± 1.5 | 27.5 ± 18.1 |
| N-acetyl-glucosamine (b) | 37.4 ± 10.5 | 30.8 ± 6.5 |
| Chondroitin sulfate © | 75.4 ± 3.6 | 38.1 ± 12.2 |
| Combination (a, b & c) | 77.7 ± 8.3 | 47.6 ± 10.0 |

Chondroitin sulfate may exert at least two beneficial actions: a) protection of the bladder mucosa, b) inhibition of mast cell activation. (Theoharides, T. C., et al., Intl. Res. Symp. On Interstitial Cystitis (Oct. 30–31, 1997), p. 35, 1997).

EXAMPLE 2

Synergistic Inhibitory Effect of Chondroitin Sulfate and Quercetin on Mast Cell Secretion and its Benefit in Gastrointestinal Conditions Here, we investigated the effect of the polysaccharide chondroitin sulfate and of the flavonoid quercetin on histamine secretion from mast cells purified from 300g male Sprague/Dawley rats. Mast cells were preincubated with the test compound for 15 min at 37° C. and washed twice prior to stimulation with 0.1 μg/ml of the mast cell secretagogue compound 48/80 (C48/80) for 10 min. Chondroitin sulfate (from shark cartilage) inhibited mast cell activation in a dose-dependent fashion with maximal inhibition of 83% at $10^{-4}$ M (Table 2); a similar effect was also seen with the naturally occurring flavonoid quercetin in vitro, but it had to be present continuously. A combination of $10^{-6}$ M chondroitin sulfate and $10^{-6}$ M quercetin exhibited a synergistic effect of about 30% inhibition even after the drugs were washed off. Rats fed 10 mg/kg body weight of each did not exhibit gastrointestinal mast cell activation in response to acute psychological stress by immobilization for 30 min. A combination of these naturally occurring products available OTC could be useful for the prevention of stress-induced gastrointestinal syndromes, such as irritable bowel syndrome or inflammatory bowel disease.

TABLE 2

Inhibition of Mast Cell Secretion, % of Total

| Conditions (n = 4) | Mast Cell Secretion (n = 3) |
|---|---|
| Control | 5.3 ± 0.4 |
| C48/80 | 31.5 ± 6.3 |
| Quercetin ($10^{-6}$M) | 30.5 ± 0.5 |
| Chondroitin sulfate ($10^{-6}$M) | 31.0 ± 2.9 |
| Chondroitin sulfate ($10^{-5}$M) | 15.3 ± 2.7 |
| Chondroitin sulfate ($10^{-4}$M) | 5.3 ± 1.3 |
| CS + Q ($10^{-6}$M) | 17.7 ± 7.1 |

EXAMPLE 3

Human Leukemic Mast Cells

Culture of human leukemic mast cells in the presence of chondroitin sulfate resulted in potent inhibition of growth, as shown below in Table 3. Cell viability was about 90% or better.

TABLE 3

Inhibition (%) of human leukemic mast cell proliferation (n = 5)

| Day | $10^{-4}$M | $10^{-5}$M | $10^{-6}$M | $10^{-7}$M |
|---|---|---|---|---|
| 3 | 57.8 ± 13.3 | 44.3 ± 12.7 | 27.2 ± 12.1 | 12.6 ± 9.6 |
| 4 | 53.1 ± 8.9 | 38.9 ± 9.1 | 25.3 ± 9.6 | 14.9 ± 6.9 |
| 5 | 52.4 ± 13.9 | 31.2 ± 15.8 | 20.7 ± 15.2 | 14.7 ± 6.8 |

Consequently, chondroitin sulfate could be useful in conditions where there is mast cell proliferation, in addition to mast cell activation, such as in systemic mastocytosis (Longley, M. D., et al., *American Academy of Dermatology* 32:545, 1995) or interstitial cystitis (Theoharides, T. C., et al, *New York Academy of Sciences* 840:619, 1998). In fact, two recent news reports recently appeared on this possibility (Theoharides, T. C., *Urology Times* Vol. 26, Mar., 1998 and Theoharides, T. C., *The Mastocytosis Chronicle* Vol. 4, winter, 1998).

EXAMPLE 4

Oral tablet

Chondroitin sulfate and kaempferol can be administered each in dosages of 50 mg to about 5.000 mg for 80 kg of body weight of the subject. A preferred embodiment for rapidly disintegrating tablets are as follows:

| Ingredients | Mg/tablet |
| --- | --- |
| Chondroitin sulfate | 2000 mg |
| Quercetin, kaempferol or mixed flavinoids | 500 mg |
| Milk sugar (12 mesh granular) | 25 mg |
| Starch | 20 mg |
| Magnesium Stearate | 0.4 mg |

EXAMPLE 5

Antiallergic Skin Cream

| Components | %/wt. | |
| --- | --- | --- |
| Chondroitin sulfate | 5.00 | |
| Kaempherol and/or quercetin | 3.00 | |
| Hydroxyzine pamoate | 4.50 | |
| Olive pit oil | 15.00 | |
| Lanolin | 1.00 | |
| Glycerin | 5.00 | |
| Methyl benzethonium chloride | 0.10 | |
| Magnesium chloride | 0.07 | |
| Ferrous sulfate | 0.001 | |
| Potassium chloride | 0.012 | |
| Sodium chloride | 0.02 | |
| Zinc oxide | 2.50 | |
| Vitamin A (retinyl palmatate) | 0.01 | (20K IU) |
| Vitamin C | 0.10 | |
| Vitamin D | 0.01 | (4K IU) |
| Vitamin E (tocopherol linoate) | 1.00 | (20K IU) |
| Sodium dihydrogen phosphate | 0.002 | |
| Nonionic emulsion base | 62.475 | |
| glyceryl monosterate | | |
| safflower oil, hybrid, 5.0% | | |
| steareth-2 | | |
| steareth-21 | | |
| stearyl alcohol | | |
| water, purified | | |
| Quaternium 15 (preservative) | 0.20 | |

THERAPEUTIC EXAMPLES

EXAMPLE 6

A 35 year old female with multiple allergies and interstitial cystitis was administered a formulation containing 200 mg chondroitin sulfate along with 1000 mg glucosamine, three soft capsules daily, for 2 months and reported almost complete reduction of her gastrointestinal symptoms of diarrhea, bloating, pain and associated skin itching.

EXAMPLE 7

A 28 year old female with systemic mastocytosis was administered a formulation containing 1,200 mg chondroitin sulfate and 500 mg mixed flavonoids for 3 months. She reported complete diappearance of her associated symptoms of gastrointestinal upset, skin redness and itching (urticaria pigmentosa) and joint pains.

EXAMPLE 8

A 42 year old male with extensive atopic dermatitis on his hands, arms and elbows applied the cream indicated in the previous section for one month with substantial reduction of redness, itching and scaling.

What is claimed:

1. A method of treating an atopic allergic disease in a mammal characterized by numbers of mast cells or levels of biochemicals secreted by said mast cells sufficiently high to cause said atopic allergic disease, comprising the step of the administration to said mammal of a phamaceutically effective amount of a proteoglycan with mast cell secretion inhibitory activity, said proteoglycan comprising a chondroitin sulfate, alone or together with one or more synergistic adjuvants.

2. The method of claim 1, wherein said adjuvant is a flavonoid.

3. The method of claim 2, wherein said flavonoid is selected from the group consisting of myrisetin, quercitin, kaempferol, genisetin, a 2-phenylchromone and 2-phenylbenzopyrone.

4. The method of claim 1, wherein said atopic allergic disease is selected from the group consisting of allergic asthma, allergic rhinitis, allergic conjunctivitis, allergic otitis media, allergic dermatitis, food allergy and allergic urticaria.

* * * * *